United States Patent [19]

Merritt

[11] Patent Number: 5,006,830
[45] Date of Patent: Apr. 9, 1991

[54] METHOD AND DEVICE FOR DETERRING THE UNAUTHORIZED REMOVAL OF A NEWBORN FROM A DEFINED AREA

[76] Inventor: Rebecca Merritt, 250 E. 700 South, Lebanon, Ind. 46052

[21] Appl. No.: 421,860

[22] Filed: Oct. 16, 1989

[51] Int. Cl.⁵ .......................... G08B 23/00; A44C 5/00
[52] U.S. Cl. ........................................ 340/573; 40/633
[58] Field of Search .................. 340/573; 40/633, 640, 40/665; 283/72, 81, 82; 235/375

[56] References Cited

U.S. PATENT DOCUMENTS

| | | | |
|---|---|---|---|
| 3,965,589 | 6/1976 | McDermott | 40/633 |
| 4,233,715 | 11/1980 | McDermott | 40/640 X |
| 4,328,978 | 5/1982 | McLaughlin | 40/640 X |
| 4,857,713 | 8/1989 | Brown | 235/375 |
| 4,899,134 | 2/1990 | Wheeless, Jr. | 240/573 |

Primary Examiner—Glen R. Swann, III
Assistant Examiner—Thomas J. Mullen, Jr.
Attorney, Agent, or Firm—David B. Quick

[57] ABSTRACT

A method and device for deterring unauthorized removal of a newborn from a defined area has a locking umbilical clamp with an attached identification mark and an attached triggering device capable of triggering a detection system upon removal of the umbilical clamp from the defined area and a wristband with an identification mark thereon corresponding to the identification mark on the umbilical clamp for attachment to the wrist of a person authorized to remove the newborn from the defined area.

15 Claims, 2 Drawing Sheets

5,006,830

METHOD AND DEVICE FOR DETERRING THE UNAUTHORIZED REMOVAL OF A NEWBORN FROM A DEFINED AREA

BACKGROUND OF THE INVENTION

FIELD OF THE INVENTION

This invention relates generally to surveillance systems and more particularly to such systems which are particularly useful to hospitals with newborns to be protected from unauthorized removal.

Theft, switching or unauthorized removal of newborns has become a great concern to hospitals and expectant parents. The need for some type of method or device to economically reduce newborn abduction or switching has resulted in the creation of various techniques or devices to deter such acts. One of the simpler, but more expensive and less effective, methods to reduce infant switching or unauthorized removal is to simply increase hospital staff in the postpartem area. The disadvantages of such a method are readily apparent. In order to overcome these disadvantages, various electronic or electo-magnetic devices have been attached to newborns and have been employed to provide warning of unauthorized removal of the newborns or a means of tracking the movements of the newborns. Therefore, various types of radio transmitters and electronic security tags or transponders have been attached to newborns to determine when the newborn has been removed from a defined area.

One example of a system for deterring unauthorized removal of a newborn which employs a radio transmitter is INFANT WATCH (c) (sic) available from Ramco Security Systems, Inc. of Gaithersburg, Md. The INFANT WATCH (c) (sic) system uses a band to attach a miniature wireless transmitter to the arm or leg of an infant and a radio receiver and alarm system to indicate when the signal from the transmitter has been lost because of unauthorized removal of the infant from the predefined area or because the band has been cut. A patient tracking system which uses a similar concept is Hawkins, et al., U.S. Pat. No. 4,814,751 issued Mar. 21, 1989. The French publication No. 2 543 715 of Mar. 30, 1983 to Mayer appears to disclose a surveillance system which likewise incorporates a radio transmitter and receiver to indicate when a child or object goes beyond a certain range.

Other newborn protection systems, e.g. SEKURMED TM available from Security Tag Systems, Inc. of St. Petersburg, Fla., use a band to attach electronic security tags to the wrist or ankle of a newborn and proximity sensors and alarms to indicate when the newborn has been removed from a predefined area. The electronic tag used in SEKURMED TM is of the type described in Charlot, Jr., U.S. Pat. No. 4,481,428 issued Nov. 6, 1984 and/or Herman, et al., U.S. Pat. No. 4,670,740 issued June 2, 1987.

Both the radio transmitter devices and the electronic tag devices described above illustrate that it is well-known in the art of newborn security to use a band to attach the devices commonly used in the electronic article surveillance industry to the wrist or ankle of a newborn. However, there are certain disadvantages in using a band to attach a security device to the wrist or ankle of a newborn. Often newborns experience weight loss immediately after birth which may result in the band loosening and falling off of the wrist or ankle. Also, a person wishing to remove a baby or switch babies could stretch or cut the bands to remove them from the baby, and thus, means to prevent this possibility need to be incorporated into the band. Also, the bands can inhibit bathing and intravenous treatment of the newborn.

It is well-known that immediately after a baby is born that its umbilical cord is typically clamped with a device called an umbilical or funis clamp. After the use of umbilical clamps became common practice, it was recognized that it was desirable to create umbilical clamps with locking features to prevent accident release and unauthorized removal of the clamp once it is attached. Examples of such clamps are described in Kariher, et al., U.S. Pat. No. 3,204,636 issued Sept. 7, 1965, Schneider, U.S. Pat. No. 3,247,852 issued Apr. 26, 1966 and Nolan, U.S. Pat. No. 4,212,303 issued July 15, 1980. The locking features of the above mentioned and other well-known umbilical clamps render such clamps desirable as a means of attaching an electronic article surveillance device to a newborn.

This invention recognizes that the use of electronic article surveillance devices with newborns is common and also recognizes that the use of locking umbilical clamps on newborns is common and combines these two uses to create a new, nonobvious device and method for protecting newborns.

SUMMARY OF THE INVENTION

One embodiment of the present invention is a device for deterring unauthorized removal of newborns from a defined area which is equipped with a detection system that generates a signal or alarm when triggered by removal of a triggering device from the defined area which comprises an umbilical clamp with a triggering device attached to it.

Another embodiment of the present invention involves clamping the umbilical cord of a newborn with an umbilical clamp containing a triggering element, providing a detection system capable of determining when the triggering element in the umbilical clamp comes within a predefined proximity of an exit from a defined area, providing an alarm system which is activated when the detection system determines that the triggering element is within the predefined proximity of an exit from the defined area and placing the newborn within the defined area.

Yet another embodiment of the present invention involves clamping the umbilical cord of a newborn with an umbilical clamp having a distinctive identification mark thereon, attaching a wristband having the same distinctive identification mark thereon to a person authorized to remove the newborn from a defined area, placing the newborn within a defined area and insuring that the distinctive identification mark on the umbilical clamp of the newborn corresponds with the distinctive identification mark on the wristband of a person wishing to remove the newborn from the defined area.

Yet another embodiment of the present invention is a system for deterring unauthorized removal and switching of newborns comprising an umbilical clamp with a distinctive identification mark thereon and a wristband with a corresponding distinctive identification mark thereon.

One object of the present invention is to deter theft of newborns from postnatal wards.

Another object of the present invention is to provide a means of attaching security devices and/or identification marks to newborns which are not easily removable.

Another object of the present invention is to provide a means of attaching security devices and/or identification marks to newborns which do not inhibit bathing.

Other objects and advantages of the present invention will be apparent from the drawings and description of the preferred embodiments.

DESCRIPTION OF THE PREFERRED EMBODIMENTS

Figure 1:
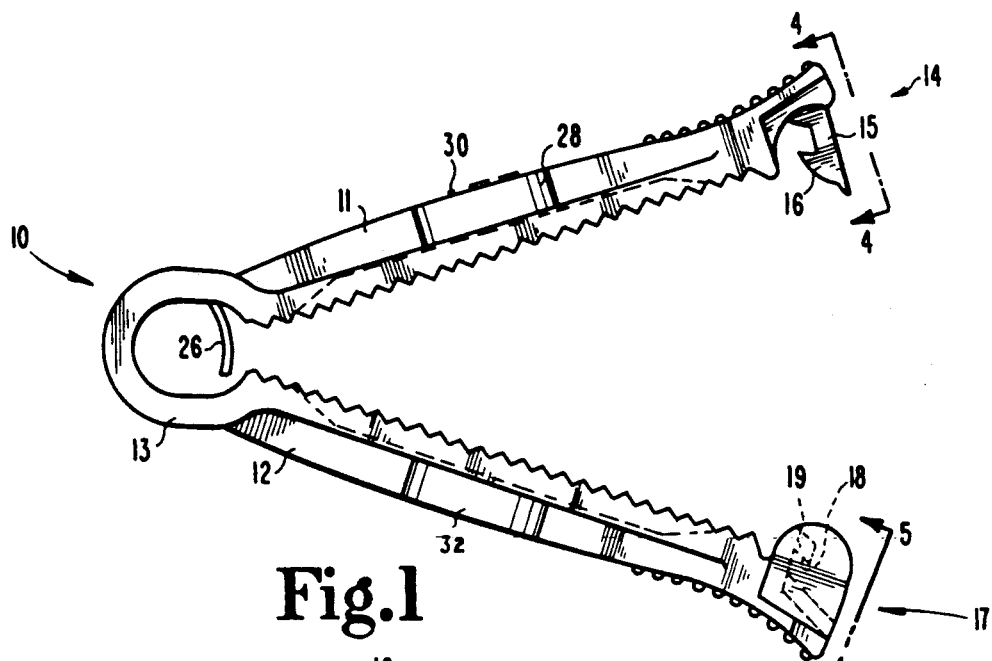
FIG. 1 is a side elevational view of an umbilical cord clamp embodying the present invention.
Figure 2:
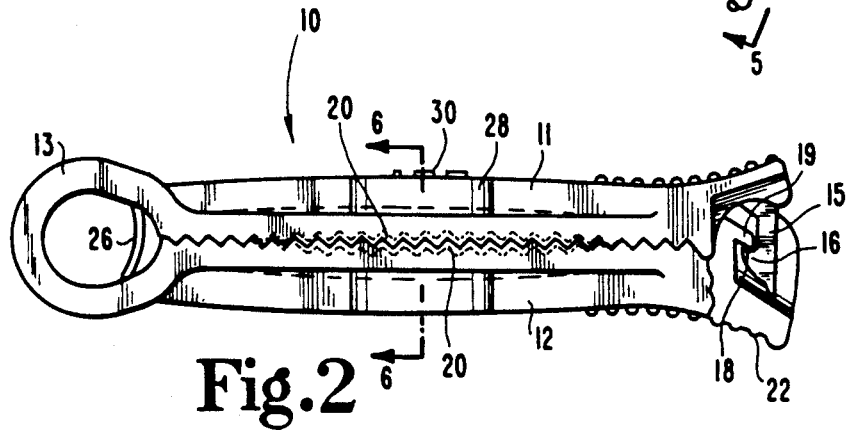
FIG. 2 is a view like FIG. 1 showing the clamp in closed position.
Figure 3:
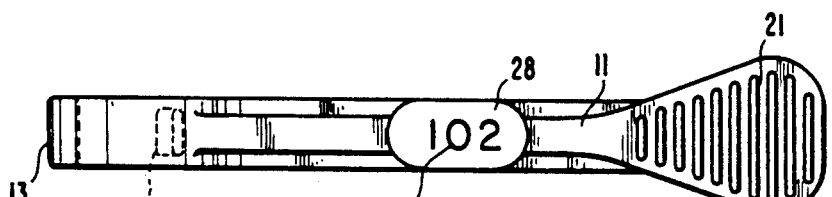
FIG. 3 is a top plan view of the clamp of FIG. 2.
Figure 4:
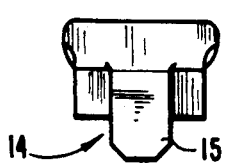
FIG. 4 is an end view taken along line 4—4 of FIG. 1.
Figure 5:
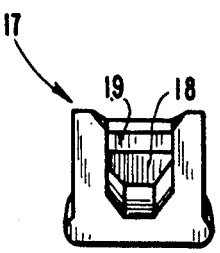
FIG. 5 is an end view taken along line 5—5 of FIG. 1.

While this invention is susceptible of embodiment in many different forms, there is shown in the drawings and will herein be described in detail specific embodiments, with the understanding that the present disclosure is to be considered as an exemplification of the principles of the invention and is not intended to limit the invention to the embodiment illustrated. The scope of the invention will be pointed out in the appended claims.

Referring to FIGS. 1-6, there is illustrated an umbilical clamp 10 which is generally V-shaped and made of a resilient, sterilizable material such as nylon. The clamp 10 has a pair of diverging arms 11 and 12 secured together at the apex of the V by an integral loop hinge 13. Locking means 14 are provided at the free end of the arm 11, the locking means taking the form of a catch with a stem portion 15 and a hook portion 16, engageable in a complementary locking portion 17 having a recess 18 and an overlying lip 19 engageable with the hook 16 as illustrated. To aid in closing the clamp, the arms 11 and 12 are provided with enlarged finger pressure portions 21 and 22, which may be grasped between the thumb and forefinger to effect a closure.

The cord clamp is provided with teeth, such as the teeth 20, to grip the umbilical cord therebetween.

Figure 6:
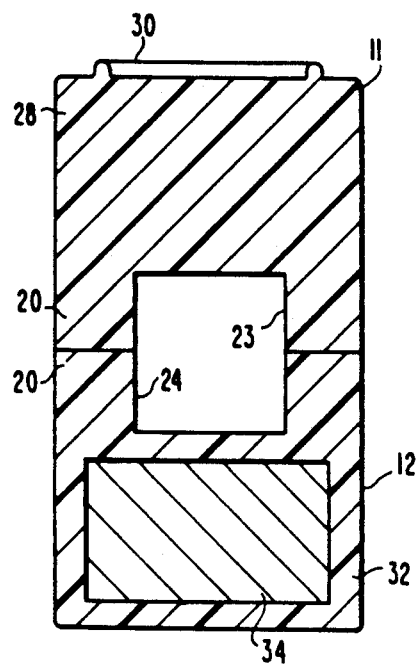
FIG. 6 is a sectional view taken along line 6—6 of FIG. 2.

To prevent the clamp from slipping off of the umbilical cord, each of the arms 11 and 12 is provided with longitudinally extending grooves 23 and 24 forming a cord-receiving channel illustrated most clearly in FIG. 6. When the clamp is closed about an umbilical cord, portions of the cord are squeezed into the cord-receiving channel and this, particularly in cooperation with the teeth 20, provides a very secure grip on the cord and the same is retained in position, even though the cord may be cut very closely adjacent the clamp.

In utilizing cord clamps having an enlarged loop portion such as the loop 13, the cord occasionally will slip into the interior of the loop through the entrance 25 as the clamp is being closed. Thus, the cord is located in an area where little or no pressure is exerted on it, or at least the pressure may be insufficient to provide an effective closure of the cord. To prevent this occurrence, the clamp 10 is provided with a blocking member 26 which is formed integrally with the loop portion 13. The blocking member is arcuate in shape and adapted to close off the entrance 25 when the clamp is in the open position of FIG. 1, so that as the clamp is moved to the closed position, entrance of the cord into the interior of the loop is prevented.

Integrally formed in the midsection of arm 11 is an enlarged oval-shaped portion 28 on which a distinctive identification mark 30 is provided. The distinctive identification mark 30 may be an integrally formed raised serial number as illustrated in the drawings or some other distinguishable mark such as bar code, color code, or letter combination. It should be obvious that each umbilical clamp in use or in stock in a hospital or health care facility should have a different distinctive identification mark thereon. For instance, if a three digit serial number is used as the distinctive identification mark, shipments of such clamps could come in a first series of 000-499 and a second series of 500-999 and the stock of first series of clamps should not be replenished until the entire stock of first series of clamps is used.

Integrally formed in the midsection of arm 12 is an enlarged oval-shaped portion 32 within which is sealed a triggering means 34 of the type commonly used in the article surveillance industry such as a marker, tag, chip, transponder, transmitter or the like. The triggering means 34 can be attached to the umbilical clamp 10 by any means which would deter removal of the triggering means 34 from the umbilical clamp. The preferred method of attachment is to imbed the triggering means in the umbilical clamp so that the triggering means is an integral part of the umbilical clamp and is totally concealed by the material used to form the clamp. The preferred triggering device is a batteryless tag such as that described in Harman, et al, U.S. Pat. No. 4,670,740, Charlot Jr., U.S. Pat. No. 4,481,428 or the Patents cited herein.

Figure 7:
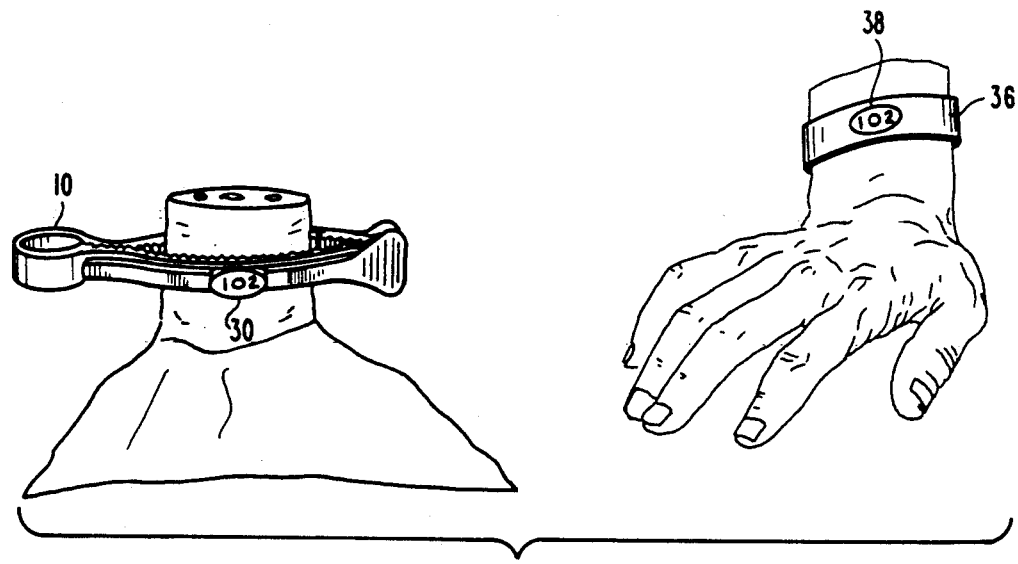
FIG. 7 is a plan view of the clamp of FIG. 1 attached to a newborn and the wristband of the present invention.

In addition to the umbilical clamp described above, a wristband 36 (FIG. 7) of the type commonly used in hospitals and health care facilities is attached to the mother or other person authorized to remove the newborn from the postnatal or other defined area. The wristband 36 has a distinctive identifying mark 38 affixed thereto or impressed thereon which corresponds to the distinctive identifying mark 30 on the umbilical clamp 10. There is a separate wristband with a corresponding distinctive identifying mark for each separate umbilical clamp. A set of wristbands with each distinctive identifying mark thereon may be provided so that a wristband may be provided to each of a plurality of persons who are authorized to remove the newborn from the defined area. Naturally, when the number of wristbands in a set with a specific identifying mark thereon exceeds the number of persons authorized to remove the newborn with the umbilical clamp having a corresponding identifying mark thereon, the excess wristbands in a set must be destroyed. Stocking of wristbands should correspond with stocking of umbilical clamps. In addition, the wristbands 36 are manufactured of stretch resistant material and are secured to the wrist with commonly used locking clamps, snaps, or sealants.

From the foregoing a method of deterring unauthorized removal of newborns from a defined area should be fairly apparent, however, the following will aid in the further understanding of the method. The hospital or health care facility wishing to deter unauthorized removal of newborns must define an area from which the newborns cannot be removed without proper authority. The boundaries of the defined area will be restricted to a certain extent by the type of detection system selected to deter removal but will typically encompass the postnatal and maternity wards or the like. A detection system and alarm or signalling system is selected that responds to the passage of a triggering device beyond the boundaries of the defined area. For instance, when the preferred embodiment of the umbilical clamp 10 is used, detection loops will be placed at each exit from the defined area. A plurality of umbilical clamps with an attached triggering device which is detectable by the selected detection system is provided. Each of the plurality of umbilical clamps provided contains a distinctive identification mark which is distinguishable from the distinctive identification mark on each of the other umbilical clamps. A plurality of sets of wristbands sized to fit the wrist of an adult are provided. Each set of wristbands contains a distinctive identifying mark thereon which corresponds with the distinctive identifying mark on one of the provided umbilical clamps. A corresponding set of wristbands is provided for each of the provided umbilical clamps.

Upon the birth of a newborn, an umbilical clamp is selected from the provided umbilical clamps and the corresponding set of wristbands is also selected. The selected umbilical clamp is used to clamp the umbilical cord of the newborn and the umbilical cord is then cut. A wristband from the selected corresponding set of wristbands is secured to the wrist of each person authorized to remove the newborn from the defined area. Any non-secured wristbands from the selected corresponding set of wristbands are destroyed. The newborn is placed within the defined area.

Unlike normal umbilical clamps which are typically removed twenty-four hours after birth, the provided umbilical clamps remain clamped to the umbilical cord of the newborn until removal of the newborn from the defined area is authorized, such as at release time. Because it is common practice to attach umbilical clamps to newborns, it will not be readily apparent that a detection system is in use. Even if an unauthorized person learns that a detection system is in use, they will be deterred from removing the umbilical clamp because of the possible deleterious consequences of early removal of a clamp. After determining that removal of the newborn from the defined area is desirable, the distinctive identification mark on the wristband of the person desiring to remove the newborn from the defined area is compared with the distinctive identification mark on the umbilical clamp on the newborn to be removed. Upon determining that the distinctive identification mark on the wristband corresponds with the distinctive identification mark on the umbilical clamp, removal is authorized, and either the umbilical clamp is cut off of or removed from the newborn, the triggering device is deactivated or the newborn is escorted beyond the boundaries of the defined area by a staff member.

The provided umbilical clamps should also contain a locking means or device and anti-slippage means to prevent or deter accidental or unauthorized intentional removal of the clamp from the umbilical cord.

What is claimed is:

1. A method for deterring unauthorized removal of newborns from a defined area comprising the steps of:

providing an umbilical clamp containing a triggering element and with a distinctive identification mark thereon;

clamping the umbilical cord of a newborn immediately after birth with the provided umbilical clamp;

providing a detection system capable of determining when the triggering element comes within a predefined proximity of an exit from the defined area;

providing an alarm system that is activated when the detection system determines that the triggering element is within the predefined proximity of an exit from the defined area; and placing the newborn with the attached triggering element within the defined area.

2. The method of claim 1 and further comprising the step of attaching a band containing a second distinctive identification mark corresponding to the distinctive identification mark on the provided umbilical clamp to a person authorized to remove the newborn to whom the provided umbilical clamp is clamped from the defined area.

3. The method of claim 2 and further comprising the step of ensuring that the distinctive identification mark on the provided umbilical clamp corresponds to the second distinctive identification mark on the attached band before authorizing the removal of the clamped newborn from the defined area by a person with the attached wristband.

4. The method of claim 1 wherein said providing an umbilical clamp step further comprises the step of providing an umbilical clamp with locking means therein and said clamping step further comprises the step of locking the provided clamp to the umbilical cord of a newborn.

5. The method of claim 4 and further comprising the step of attaching a band containing a second distinctive identification mark corresponding to the distinctive identification mark on the provided umbilical clamp to a person authorized to remove the newborn to whom the provided umbilical clamp is clamped from the defined area.

6. The method of claim 5 and further comprising the steps of ensuring that the distinctive identification mark on the provided umbilical clamp corresponds to the second distinctive identification mark on the attached band before authorizing the removal of the clamped newborn from the defined area by a person with the attached wristband.

7. A device for deterring unauthorized removal of newborns from a defined area which is equipped with a detection system that generates a signal or alarm when triggered by removal of a triggering means from the defined area comprising:

an umbilical clamp means for clamping the umbilical cord of a newborn;

a distinctive identification mark attached to said umbilical clamp means; and triggering means attached to said umbilical clamp means for triggering the detection system upon removal of the umbilical clamp means from the defined area.

8. The device of claim 7 wherein said umbilical clamp means further comprises a locking means for locking said umbilical clamp to an umbilical cord of a newborn.

9. The device of claim 8 wherein said triggering means is integrally formed into said umbilical clamp means.

10. A method for deterring unauthorized removal of a newborn from a defined area comprising the steps of:
  providing an umbilical clamp with a distinctive identification mark thereon;
  providing a band with a second distinctive identification mark thereon which corresponds with the distinctive identification mark on the provided clamp;
  clamping the umbilical cord of a newborn with the provided clamp;
  attaching the provided band to a person authorized to remove the clamped newborn from the defined area;
  placing the clamped newborn in the defined area; and
  ensuring that the distinctive identification mark on the umbilical clamp of the clamped newborn corresponds with the second identification mark on the band attached to a person wishing to remove the clamped newborn from the defined area prior to authorizing the removal of the newborn from the defined area.

11. The method of claim 10 and further comprising the step of locking the provided umbilical clamp to the umbilical cord of the clamped newborn.

12. The method of claim 11 wherein the provided umbilical clamp has a triggering device attached thereto and further comprising the step of providing a detection device capable of remotely determining when the triggering device in the provided umbilical clamp is removed from the defined area.

13. A device for deterring removal of a newborn from a defined area except by an authorized person comprising:
  umbilical clamp means for clamping the umbilical cord of a newborn;
  distinctive identification means attached to said umbilical clamp means for distinguishing the umbilical clamp means from other umbilical clamps;
  wristband means for attachment to the wrist of a person authorized to remove the newborn from the defined area; and
  corresponding distinctive identification means attached to the wristband means for distinguishing the wristband means from other wristbands and for providing a correspondence with the distinctive identification means attached to said umbilical clamp means.

14. The device of claim 13 wherein said distinctive identification means is an integral part of said umbilical clamp means.

15. The device of claim 13 and further comprising locking means attached to said umbilical clamp means for locking said umbilical clamp means to an umbilical cord of a newborn.

* * * * *